US010450542B2

(12) United States Patent
Vulto et al.

(10) Patent No.: US 10,450,542 B2
(45) Date of Patent: Oct. 22, 2019

(54) APPARATUSES FOR AND METHODS OF PROCESSING CELLS AND RELATED STRUCTURES

(75) Inventors: Paul Vulto, The Hague (NL); Sebastiaan Johannes Trietsch, The Hague (NL); Heiko Jan van der Linden, Amsterdam (NL); Adrianus Theodorus Joore, Utrecht (NL); Thomas Hankemeier, Leiden (NL)

(73) Assignee: UNIVERSITEIT LEIDEN, Leiden (NL)

( * ) Notice: Subject to any disclaimer, the term of this patent is extended or adjusted under 35 U.S.C. 154(b) by 0 days.

(21) Appl. No.: 14/003,620

(22) PCT Filed: Mar. 8, 2012

(86) PCT No.: PCT/EP2012/054056
§ 371 (c)(1),
(2), (4) Date: Nov. 15, 2013

(87) PCT Pub. No.: WO2012/120102
PCT Pub. Date: Sep. 13, 2012

(65) Prior Publication Data
US 2014/0065597 A1    Mar. 6, 2014

(30) Foreign Application Priority Data
Mar. 8, 2011    (GB) .................................. 1103917.9

(51) Int. Cl.
*C12M 1/00*    (2006.01)
*B01F 13/00*    (2006.01)
(Continued)

(52) U.S. Cl.
CPC ......... *C12M 27/18* (2013.01); *B01F 13/0083* (2013.01); *B01L 3/502746* (2013.01);
(Continued)

(58) Field of Classification Search
CPC ...... C12M 27/18; C12M 23/16; C12M 23/34; C12M 29/10; C12M 35/08;
(Continued)

(56) References Cited

U.S. PATENT DOCUMENTS 4,225,671 A     9/1980 Puchinger et al.
6,296,020 B1 * 10/2001 McNeely et al. ............. 137/806
(Continued)

FOREIGN PATENT DOCUMENTS

EP      0112155         6/1984
WO      2008/028241     3/2008
WO      2010/086179     8/2010

OTHER PUBLICATIONS

David Juncker, et. al., "Soft and rigid two-level microfluidic networks for patterning surfaces" (2001), J. Micromech. Microeng 11, pp. 532-541 (Year: 2001).*

(Continued)

*Primary Examiner* — William H. Beisner
*Assistant Examiner* — Danielle B Henkel
(74) *Attorney, Agent, or Firm* — Nixon Peabody LLP; Ronald I. Eisenstein; Nicole D. Kling

(57) ABSTRACT

Apparatus for processing life-based organic particles, including particles selected from the list comprising cells, cellular spheroids, tissues, eukaryotes, micro-organisms, organs or embryos, comprises a hollow volume (10) that (a) is internally divided into at least first (14), second (16) and third (17) sub-volumes by at least two phaseguides (12, 13) formed inside the volume and (b) includes parts that are relatively upstream and relatively downstream when judged with reference to the movement of a meniscus or a bulk liquid in the volume (10). The apparatus includes at least first, second and third fluid conduits (19, 21, 22) connected to permit fluid communication between the upstream exte- (Continued)

rior of the volume (10) and a respective said sub-volume (14, 16, 17); and at least one further conduit (24) connected to permit fluid communication between the downstream exterior of the volume (10) and a said sub-volume. The first sub-volume (14) contains one or more life-based particles supported in or by a gel or gel-like substance; and the second sub-volume (16) communicates with the first sub-volume so as to permit transport of substances between the first and second sub-volumes (14, 16) and contains at least one gel or gel-like substance.

17 Claims, 5 Drawing Sheets

(51) Int. Cl.
*B01L 3/00* (2006.01)
*C12M 3/06* (2006.01)
*C12M 1/42* (2006.01)

(52) U.S. Cl.
CPC .............. *B01L 3/56* (2013.01); *C12M 23/16* (2013.01); *C12M 23/34* (2013.01); *C12M 29/10* (2013.01); *C12M 35/08* (2013.01); *B01L 2200/0605* (2013.01); *B01L 2200/0621* (2013.01); *B01L 2200/0684* (2013.01); *B01L 2300/087* (2013.01); *B01L 2300/089* (2013.01); *B01L 2300/0816* (2013.01); *B01L 2300/0851* (2013.01); *B01L 2300/0864* (2013.01); *B01L 2300/0867* (2013.01); *B01L 2300/161* (2013.01); *B01L 2400/0406* (2013.01); *B01L 2400/0688* (2013.01); *B01L 2400/086* (2013.01); *B01L 2400/088* (2013.01); *Y10T 137/0318* (2015.04)

(58) Field of Classification Search
CPC .. B01F 13/0083; B01L 3/56; B01L 3/502746; B01L 2200/0605; B01L 2200/0621; B01L 2200/0684; B01L 2300/0816; B01L 2300/0851; B01L 2300/0864; B01L 2300/0867; B01L 2300/087; B01L 2300/089; B01L 2300/161; B01L 2400/0406; B01L 2400/0688; B01L 2400/086; B01L 2400/088

See application file for complete search history.

(56) References Cited

U.S. PATENT DOCUMENTS

| | | | |
|---|---|---|---|
| 2002/0182747 A1* | 12/2002 | Beebe | B01L 3/5027 436/180 |
| 2003/0005877 A1* | 1/2003 | David | C30B 7/00 117/68 |
| 2004/0028566 A1 | 2/2004 | Ko et al. | |
| 2007/0280856 A1 | 12/2007 | Ulmanella et al. | |
| 2008/0160502 A1* | 7/2008 | Barnes | B01L 3/502723 435/4 |
| 2009/0117170 A1* | 5/2009 | Kroehne et al. | 424/424 |
| 2010/0084270 A1* | 4/2010 | Vulto | B01L 3/502753 204/461 |
| 2010/0089529 A1 | 4/2010 | Barholm-Hansen et al. | |
| 2010/0300563 A1* | 12/2010 | Ramunas | G01N 35/00 137/565.01 |

OTHER PUBLICATIONS

Vulto et al., Journal of Micromechanics & Microengineering, 16(9):1847-1853 (2006). "Selective sample recovery of DEP-separated cells and particles by phaseguide-controlled laminar flow; selective sample recovery of DEP-separated particles."

Trietsch et al. "Microfluidic titer plate for stratified 3D cell culture" Royal Society of Chemistry: Lab Chip 13:3548 (2013).

* cited by examiner

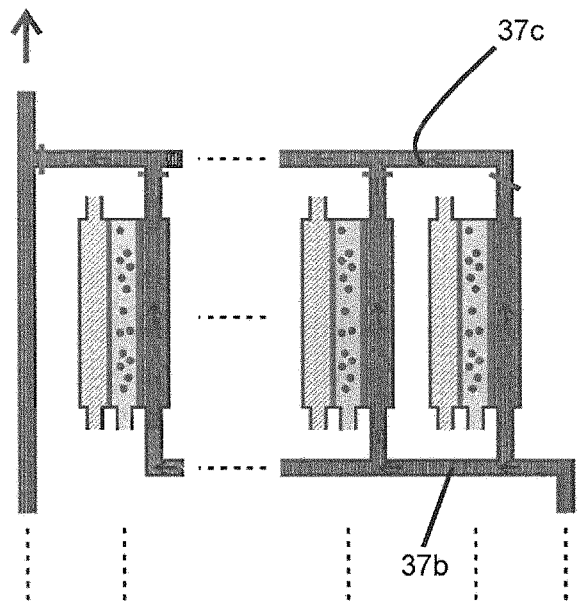
Figure 5a
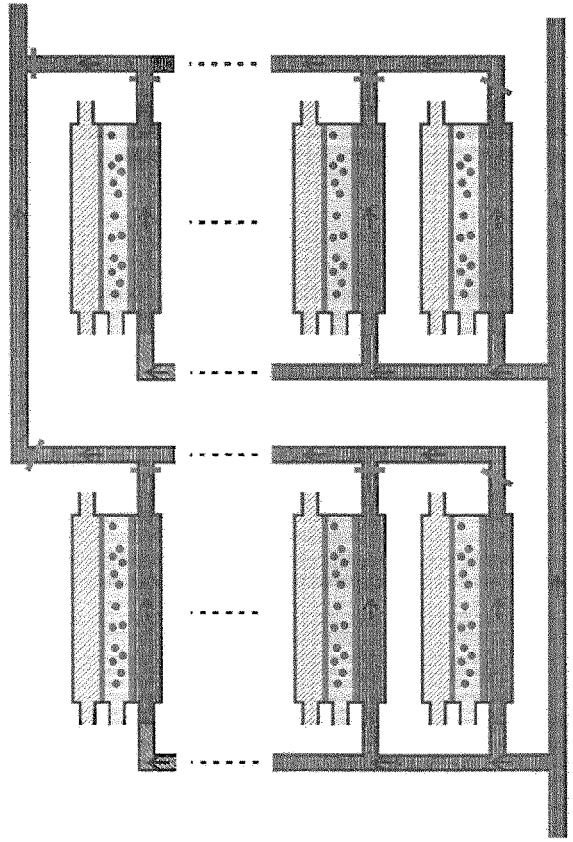
Figure 5b
Figure 5c

APPARATUSES FOR AND METHODS OF PROCESSING CELLS AND RELATED STRUCTURES

CROSS REFERENCE TO RELATED APPLICATIONS

This application is a 35 U.S.C. § 371 National Phase Entry Application of International Application No. PCT/EP2012/054056 filed Mar. 8, 2012, which designates the United States, and which claims benefit of Great Britain Application No. 1103917.9 filed Mar. 8, 2011, the contents of each of which are incorporated herein by reference in their entireties.

The invention relates to apparatuses for and methods of processing cells, cellular spheroids, tissues, eukaryotes, micro-organisms, organs, organic enzymes, gene sequences/chains, proteins or embryos, referred to herein for convenience as "life-based organic particles". The term "life-based organic particles" potentially includes other structures than those listed. The definition of "life-based organic particles" as used herein therefore is not limiting of the scope of the invention as claimed.

There is strong scientific and commercial interest in the cultivation of life-based organic particles in laboratory situations closely mimicking the conditions that such particles would encounter in a complex living organism such as but not limited to a mammal.

The reasons for this interest are well known. It has for many years been desirable to avoid whenever possible the studying of e.g. cells, tissue and organs in vivo. Aside from the fact that this is often very expensive and associated with understandably burdensome regulatory requirements the results of studies in living creatures may exhibit high variability from one candidate to the next; and they sometimes present risks to the candidates on which the studies are carried out.

Moreover the compounds, reagents and other substances forming the subject of study may be difficult to administer correctly to locations in the human or animal body; and the quantities of such substances required for effective dosing using living study samples may be very high.

In recent decades therefore various branches of the scientific community have sought to create laboratory environments in which cells, tissues, organs, micro-organs, embryos and in some cases eukaryotes can be studied away from animal bodies.

Numerous designs of cultivation chamber, tissue scaffold and related apparatuses have been created as a result. It has however been found that seeking to cultivate e.g. tissues or organs in conditions that do not accurately replicate in-vivo situations can lead to various serious flaws in experiments and observational activities.

One example, of many, falling in to this category concerns the influence of flat surfaces of cultivation chambers on cells that in the natural condition do not contact such surfaces. Another ever-constant problem concerns the need to supply living cells with a constantly replenished supply of nutrients, oxygen, enzymes and so on; and to remove from the vicinity of cells waste products, metabolites, respiration products and similar substances. In natural environments e.g. a blood supply or lymphatic system may provide these functions but they are very difficult to replicate with accuracy in laboratory equipment intended for cell cultivation.

Many other instances of experimental defect will be known to and recognised by workers of skill in the art.

Therefore there is a need for apparatuses that accurately mimic in vivo conditions when studies are carried out on life-based organic particles of the kinds indicated above.

Moreover there is an increasing requirement for tests, assays, reactions, experiments and related activities to be carried out on a large scale (for example involving many hundreds of samples that are completed simultaneously or in accordance with a controlled sequence). Many existing laboratory apparatuses fail to provide these advantages.

It is known to use so-called phaseguides in the construction of equipment intended to contain and control liquids and liquid-based substances.

A phaseguide may be defined as a structure, in a volume that is to be filled with or emptied of a liquid, that limits the ability of the meniscus of a body of liquid to advance or recede in the volume, thereby defining an interface between the liquid and another substance (i.e. another liquid, or a gas) that is of predetermined shape.

Phaseguides may be constructed in a variety of ways. One technique involves constructing a sharp edge. Advancement over such a sharp edge requires a change of the principal radii of a fluid-fluid meniscus, leading to a higher pressure drop over the meniscus thus representing a pressure barrier. This concept is also known as "meniscus pinning".

A typical phaseguide is therefore a three-dimensional structure that protrudes into the liquid along the complete length of the meniscus. Pinning of the meniscus on the resulting, elongate protrusion requires such additional energy for the liquid meniscus to cross it that the liquid is confined unless additional energy is applied to the body of liquid.

Another typical phaseguide is a ridge protruding into the bulk material. In this case pinning occurs before the phaseguide.

In addition, the phaseguide may include a usually deliberate location of weakness at which the energy required to cross the phaseguide is lower. At such a location the liquid may, if the phaseguide is properly designed, cross the phaseguide. This deliberate location of weakness also defines the "stability" of a phaseguide, which determines the order or priority of phaseguide overflow when a bulk liquid faces multiple phaseguides simultaneously during meniscus advancement or recession.

A particularly versatile phaseguide is created when the substrate facing the phaseguide is more hydrophilic than the phaseguide itself. Such an implementation leads to stretching of the meniscus and increases the effect that angles and their radii have on the stability of a phaseguide.

Thus the phaseguides may, depending on their precise design, either confine a liquid completely; or may permit its advancement or recession only at a preferred location so that the liquid follows a chosen path, fills or empties a particular space in the volume, or adopts a particular shape.

Phaseguides may instead of being constructed as protruding barriers be defined by areas on an internal surface of a volume that are of differing degrees of wettability. Again such areas may cause a requirement for the input of energy in order to encourage a liquid meniscus to advance across them.

Numerous designs of phaseguide structure are disclosed in WO2010/086179 A2. An understanding of this publication is desirable from the standpoint of explaining the invention, so the entire content of WO2010/086179 is incorporated herein by reference.

Phaseguides that operate to confine liquids nonetheless may be arranged to permit controlled crossing, by the liquid, of the barrier represented by the phaseguide; and/or mixing of two liquids confined on opposite sides of a phaseguide or a combination of phaseguides that define an interposed barrier structure. Arrangements for achieving these effects are described in WO2010/086179 WO2010/085279, in which the concept of a "confining phaseguide", that is of particular utility in embodiments of the invention described herein, is explained in detail.

According to the invention in a first aspect there is provided apparatus for processing life-based organic particles including but not limited to cells, cellular spheroids, tissues, eukaryotes, micro-organisms, organs or embryos, the apparatus comprising a hollow volume that (a) is internally divided into at least first, second and third sub-volumes by at least two phaseguides formed inside the volume and (b) includes parts that are relatively upstream and relatively downstream when judged with reference to the movement of a meniscus or a bulk liquid in the volume, the apparatus including at least first, second and third fluid conduits connected to permit fluid communication between the upstream exterior of the volume and a respective said sub-volume; and at least one further conduit connected to permit fluid communication between the downstream exterior of the volume and a said sub-volume, the first said sub-volume containing one or more life-based particles supported in or by a gel or gel-like substance; and the second sub-volume communicating with the first sub-volume so as to permit transport of substances between the first and second sub-volumes and containing at least one gel or gel-like substance.

An advantage of this arrangement is that it becomes possible to create truly realistic cultivation environments in laboratory situations while also providing the possibility of performing very large-scale assays and trials as described above. The apparatus of the invention therefore addresses the drawbacks and requirements set out herein.

Optional aspects of the invention are defined in the dependent claims.

The invention is also considered to reside in a method of processing cells, cellular spheroids, tissues, eukaryotes, micro-organisms, organs or embryos comprising the steps of:
a. charging the first volume of apparatus in accordance with the invention as claimed herein with a quantity of a gel or gel-like substance containing or supporting one or more cells, cellular spheroids, tissues, eukaryotes, micro-organisms, organs or embryos;
b. permitting or causing gelation of the gel or gel-like substance;
c. charging at least the second sub-volume with a gel or gel-like substance; and
d. causing or permitting fluid communication between the first and second sub-volumes.

A further method according to the invention includes the steps of:
a. charging the first volume of apparatus according to claim 15 hereof with a quantity of a gel or gel-like substance containing or supporting one or more cells, cellular spheroids, tissues, eukaryotes, micro-organisms, organs or embryos;
b. charging at least the second sub-volume with a gel or gel-like substance; and
c. causing or permitting fluid communication between the first and second sub-volumes.

There now follows a description of preferred embodiments of the invention, by way of non-limiting example, with reference being made to the accompanying drawings in which.

Figures 3A, 3B:
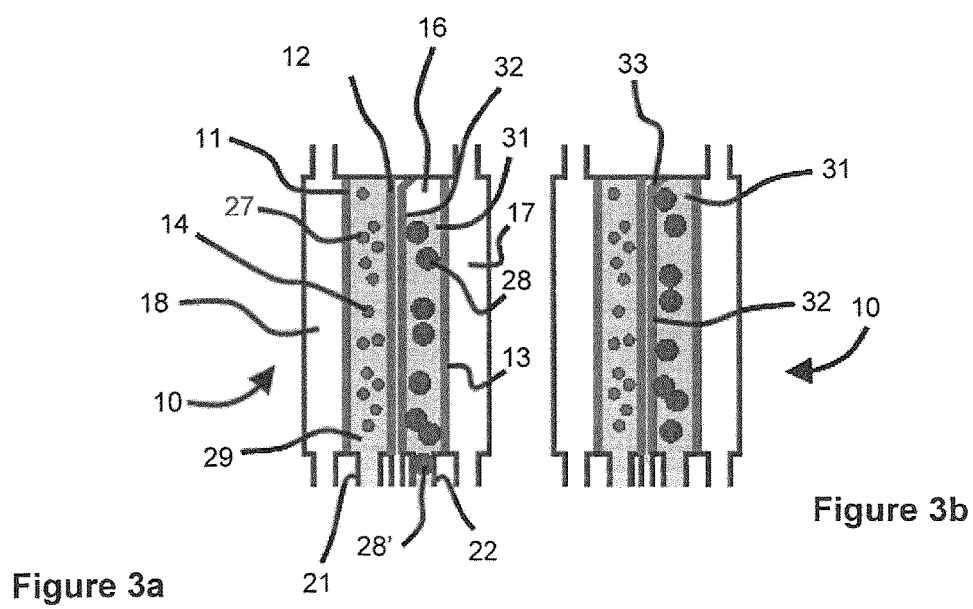
Figure 4A:
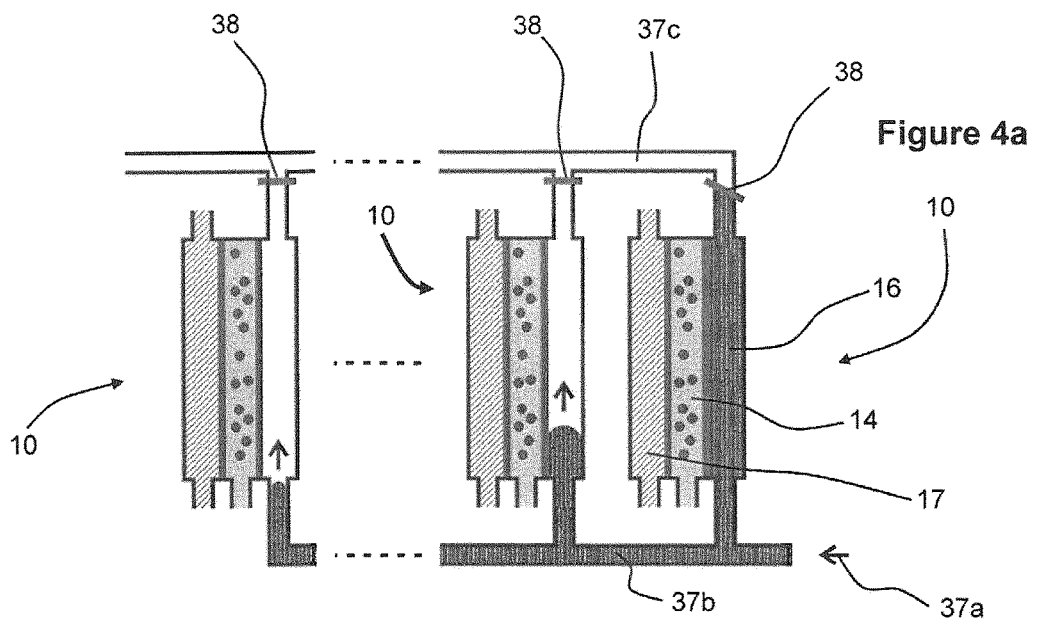
Figure 4B:
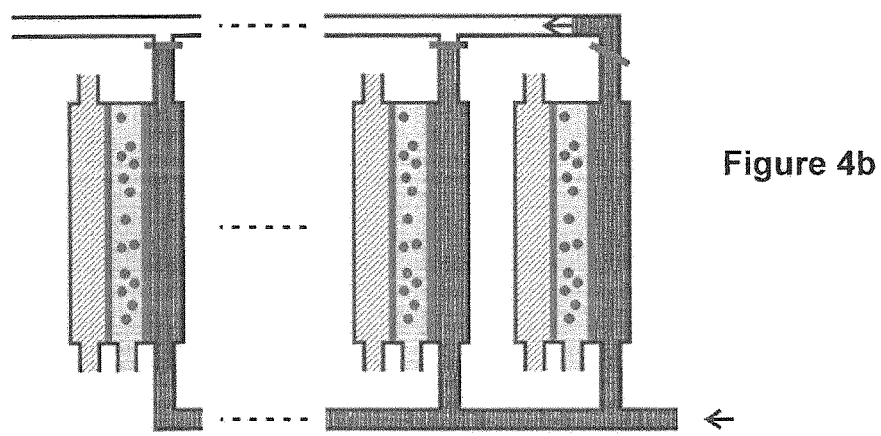
Figure 4C:
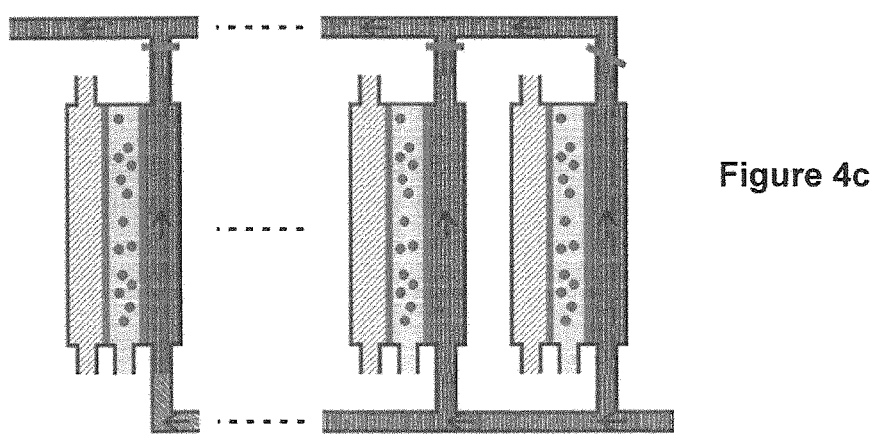

FIGS. 3*a* and 3*b* shows two states of filling of a further embodiment of apparatus according to the invention;

FIGS. 4*a*-4*c* show in schematic form three states of filling of a further, more complex apparatus according to the invention; and FIGS. 5*a*-5*c* are similar views to FIGS. 4*a*-4*c* showing the construction and use of an apparatus according to the invention that is suitable for so-called "one shot" perfusion of life-based organic particles in a complex array of cultivation chambers.

Figure 1:
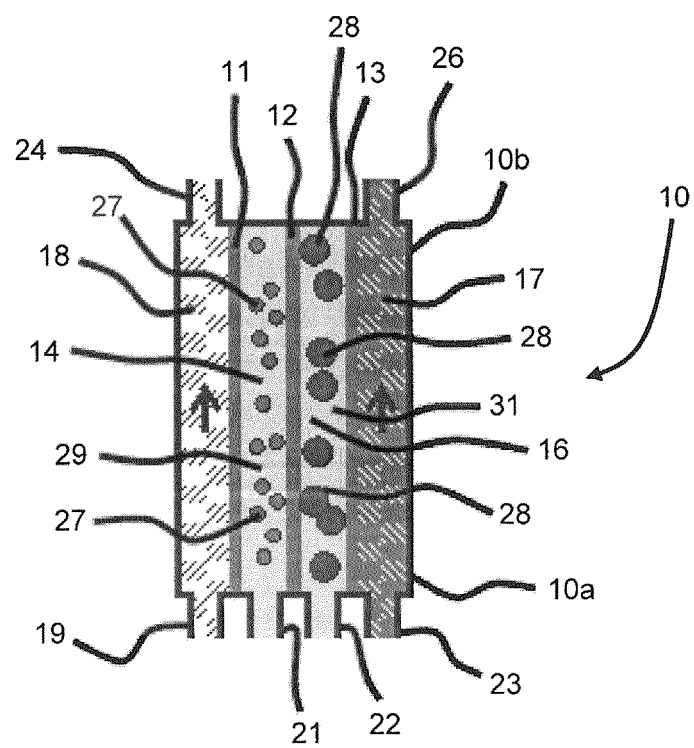
FIG. 1 is a schematic, horizontally sectioned view of one form of apparatus in accordance with the invention.

Referring to the drawings, in FIG. 1 a hollow cuboidal volume 10 constructed in any of a number of ways known in the art of phaseguide chamber technology for example as described in WO2010/086179 A2 is in the embodiment shown internally divided by first, second and third phaseguides 11, 12, 13 into four stripe-like sub-volumes 14, 16, 17, 18.

In the illustrated embodiment of the invention the sub-volumes 14, 16, 17, 18 are shown extending from one end of the interior of the volume 10 to the other in parallel with one another. The sub-volumes are rectangular in plan view and would have a vertical extent in a direction perpendicular to those visible in FIG. 1.

The volume 10 and the sub-volumes 14, 16, 17, 18 may adopt other shapes and forms as required. The phaseguides 11, 12, 13 need not follow the straight line patterns shown and may be curved or part-polygonal for example. An enormous variety of phaseguide, volume and sub-volume shapes, orientations, sizes and arrangements is possible within the scope of the invention, with the FIG. 1 arrangement being employed as merely an illustrative example.

It is preferable that the interiors of the sub-volumes may be observed in some experiment-based fashion, and especially optically. To this end the sub-volumes may include transparent or translucent walls or windows as is known to the worker of skill. In some embodiments one or more of the sub-volumes may be open on e.g. an in-use upper side, but in the majority of practical embodiments the volume 10 would be substantially closed in order to isolate the experimental environment from ambient conditions that might otherwise induce evaporation, temperature changes or contamination.

The two sub-volumes 14, 16 extending respectively to either side of the end-to-end centre line of the volume 10 occupied by phaseguide 12 are herein designated the first and second sub-volumes. The sub-volumes 17, 18 lying horizontally outwardly of the first and second sub-volumes 14, 16 are designated third and fourth sub-volumes respectively.

Each of the sub-volumes 14, 16, 17, 18 includes connected thereto at one end 10*a* designated the upstream end when considering filling of the sub-volumes with fluids a respective fluid conduit 19, 21, 22, 23. The designs of the conduits may vary significantly within the scope of the invention but their main function is to permit fluid communication between sources of fluids (not shown) located externally of the sub-volumes; and the insides of the sub-volumes 14, 16, 17, 18.

At the opposite, herein downstream, (when judged with reference to filling of the sub-volumes 14, 16, 17, 18) end 10b of the volume 10 each of the third and fourth sub-volumes 16, 17 is connected to a further respective conduit 24, 26.

The conduits 19, 23 function to supply nutrients, oxygen, medium, plasma and/or a range of further fluids to life-based organic particles in the sub-volumes 14, 16 as described below; and the further conduits 24, 26 are intended to transport depleted medium, depleted buffer, depleted plasma, waste products, respiration products, metabolites and so on away from such particles.

To this end the first sub-volume 14 contains a gel or gel-like substance 29 that supports one or more life-based particles 27 illustrated schematically in FIG. 1. The gel 29 may be chosen to provide a physical support for the particles 27 and also to provide a correct biochemical environment for cultivation and/or viability of the particles for the duration of a study.

Examples of gels or gel-like substances that are suitable for use in the sub-volumes of the invention include but are not limited to basal membrane extract, human or animal tissue, cell culture-derived extracellular matrices, animal tissue-derived extracellular matrices, synthetic extracellular matrices, hydrogels, collagen, soft agar, egg white and commercially available products such as Matrigel®.

The second sub-volume 16 contains a second gel or gel-like substance, or a non-gel liquid, 31 that may be similar to substance 29 or may differ therefrom, depending on the requirements of the experiment. Substance 31 may contain chemicals, nutrients or pharmaceuticals the effect on the particles 27 it is required to investigate, or (for example) further life-based particles 28 represented schematically in FIG. 1. A wide variety of material choices is possible within the scope of the invention.

The phaseguide 12 separating sub-volumes 14 and 6 from one another typically in accordance with the invention is a confining phaseguide such as those described in WO2010/085279A2. A characteristic of such phaseguides is that they can be designed to permit controlled mixing, diffusion or perfusion of the substances in the adjacent sub-volumes 14, 16.

Thus as just one example of use of the apparatus of FIG. 1 the gel, etc, 31 in second sub-volume 16 may contain cells 28 that interact with e.g. cells 27 in first sub-volume 14. The combination of cells 27 in first sub-volume 14 and cells 28 in sub-volume 16 thereby are combined in a manner that accurately replicates an in vivo situation.

As another example of use of the apparatus of FIG. 1 the gel, etc, 31 in second sub-volume 16 may contain a chemical compound that affects e.g. cells 27 in first sub-volume 14 under investigation. The cells 27 in first sub-volume 14 thereby may become dosed in a manner that accurately replicates an in vivo situation, with the cells supported in a gel or gel-like substance the density, viscosity composition of which mimic the media in which the cells would naturally exist.

Another option is for the transport of life-based particles from the first sub-volume into the second sub-volume to occur, as a result of the existence of a gradient including but not limited to a gradient in chemical concentration, chemical composition, temperature, pressure, electric field, light, nutrients, oxygen, gel density and gel composition The arrangement of the invention therefore evidently solves some of the long-standing drawbacks of the prior art.

Maintaining the viability of cells in an experimental situation is often difficult. The purpose of the sub-volumes 17 and 18 is to provide for the transport, in a continuous flow via conduits 19 and 24 (in the case of sub-volume 18) and 23 and 26 (in the case of sub-volume 17), of nutrients, oxygen, carbon dioxide, growth factors, other proteins, signalling molecules, compounds, further cells and the like into the vicinity of the sub-volumes 14, 16; and the transport away of waste products, metabolites and the like. This activity is indicated by the arrows in FIG. 1. The arrangement of the invention provides for considerable improvements in cell, etc, viability than prior art arrangements.

To this end the conduits 19, 24, 23, 26 could be connected for example in liquid pumping/supply circuits the nature and operation of which will be known to the worker of skill.

The sub-volumes 17, 18 need not contain the same substances; and in many cases the substances transported in the two sub-volumes 17, 18 will differ from one another.

The phaseguides 11, 13 in view of the foregoing are respectively arranged to permit or promote the transport of liquids or other substances into and/or out of the sub-volumes 14, 16 from/to the sub-volumes 18, 17. These phaseguides therefore also could be confining phaseguides of the kind described in WO2010/086179 A2.

Another mode of use of the apparatus of the invention might relate to the cultivation, etc, of cells in proximity to one another (without a requirement for transport of life-based particles from one sub-volume to another). It is apparent that the FIG. 1 apparatus readily could be employed in this manner, with the cells, etc, 27, 28 maintained in the respective first 14 and second 16 sub-volumes for the duration of an experiment.

Examples of cell types that may be co-cultured in the ways described herein, using the apparatus of the invention, include co-cultures of e.g. cancer cells with cancer associated fibroblasts (CAFs); liver cells with any other cells or tissues; cartilage with osteoblast; various cell types present in colon and intestinal cells; endothelial blood vessel cells in combination with any other cell type, including such cell combinations derived from the brain functioning as ex-vivo blood-brain barriers; skin cells; cells involved in lung tissue; and combinations of cells excreting hormone or other signaling factors and target tissues.

The co-cultures may contain gradients of differentiating cells, for example differentiation gut crypt cells; and embryonic cells such as endo-, meso- and ectoderm, stem cells. For the avoidance of doubt however to the extent that this patent application gives rise to rights in a jurisdiction that does not support the grant of patent rights in respect of human embryonic stem cells such cells obtained from human embryos; their use; and treatments of human embryos are excluded from the scope of protection under the claims hereof.

Concentration gradients of hormones, nutrients growth factors, gases or any cell-cell, tissue-tissue or organ-organ signaling factors can through use of the invention be established across cultured cells, thus exposing the cells to said signaling factors, hormones, nutrients or gases according to their position in the established gradient.

In another arrangement according to the invention the sub-volumes 17, 18 could contain chemicals the flow rates and concentrations of which are such as to establish a concentration gradient from one side of the first sub-volume 14 to the other (as viewed in FIG. 1) or, through judicious arrangement of the fluid flow rates in sub-volumes 17, 18, from one end of the first sub-volume 14 to the other.

In particular in this regard at low flow rates in sub-volumes 17, 18 it becomes possible to maintain concentration gradients across the sub-volume 14 and if present (see below) the sub-volume 17 that are generally constant from one end of the sub-volumes 14, 16 to the other. At higher rates of flow the concentration gradient across the sub-volumes 14, 16 may be arranged to vary from one end of the sub-volumes to the other. As an example of this, a high concentration gradient may be arranged to exist adjacent the conduits 21, 22 and a lesser concentration gradient at the opposite end of the sub-volumes 14, 16.

Another possibility is to arrange for the flow of liquid in the sub-volumes 17, 18 respectively to be in opposite directions, such that one of the arrows in FIG. 1 would be reversed. As a result particular gradient profiles may be developed in the sub-volumes.

Another possibility is to arrange for the flow of liquid in the sub-volumes 17, 18 not to be alongside the first and second sub-volume regions, and instead passing through the sub-volume regions.

Yet another option is to arrange for the liquid in sub-volume 17 and sub-volume 18 to be static during an experiment. As a result a concentration gradient may be established in the sub-volumes 14, 16 that alters over time until an equilibrium exists.

If in the alternative only one of the sub-volumes 17, 18 contains a static liquid the concentration of a compound in the other sub-volume 17, 18 would alter over time as its contents become increasingly dilute owing to material transport across the phaseguides illustrated.

The sub-volumes 17, 18 could in some embodiments within the scope of the invention contain gases or sets of immiscible liquids.

A greater number of the sub-volumes could be defined within the volume 10 if desired. Moreover the insides of the various sub-volumes could themselves be sub-divided for example by one or more phaseguides of the "contour" type that as described in WO2010/086179 A2 can assure a particular pattern of filling of a volume with a fluid. One particular option that is thereby made possible is the stratification of substances inside one or more of the sub-volumes.

The sub-volume 17 and associated conduits 23, 26 may be omitted from some embodiments of the invention.

The foregoing arrangement therefore represents the most rudimentary version of the invention that is presently known to the inventors.

Use of the apparatus of FIG. 1 typically would involve firstly supplying a gel or gel-like substance, containing life-based particles of experimental interest, via conduit 21 into sub-volume 14. Thereafter it would be necessary to await gelation of the gel before carrying out a similar activity in respect of sub-volume 16, since otherwise the body of gel in sub-volume 14 may not be sufficiently stable as to permit the commencement of experimentation.

Once stable conditions are established in the sub-volumes 14, 16 the flow of fluids by way of conduits 19, 24, 23, 26 may commence in accordance with the protocol of the experiment of interest.

Figure 2:
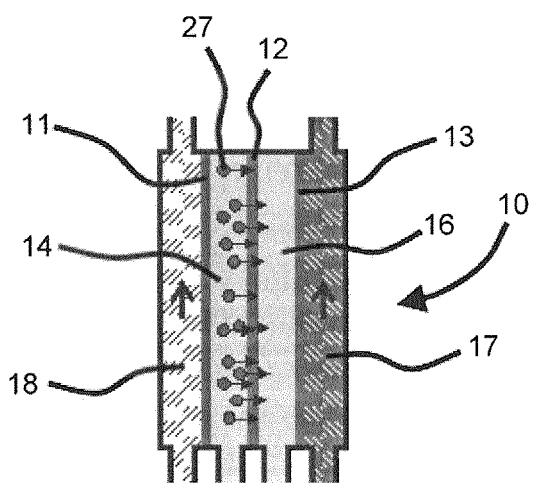
FIG. 2 is a view similar to the FIG. 1 illustration of another embodiment of apparatus according to the invention.

Referring now to FIG. 2 there is shown an apparatus that is similar to the FIG. 1 apparatus but is configured to promote the transport of life-based particles, and especially cells 27, from the first sub-volume 14 into the second sub-volume 16. Such transport is signified by arrows in FIG. 2.

In the embodiment of FIG. 2 the second sub-volume 16 is shown devoid of life-based particles but this need not necessarily be the case.

A variant on this arrangement is one in which an additional sub-volume may be defined inside volume 10 and allowing for the cells 27 in sub-volume 14 to grow or migrate into one or both of two adjacent sub-volumes, or from outer sub-volumes towards each other in inner sub-volumes. This migration may be a result of a gradient including but not limited to a gradient in chemical concentration, chemical composition, temperature, pressure, electric field, light, nutrients, oxygen, gel density and gel composition. This may result in production of e.g. a scratch assay, invasion assay, migration assay or wound healing assay.

Use of the FIG. 2 apparatus is similar to that of FIG. 1, in that it involves the sequential injection of gel-like substances into the sub-volumes 14, 16 with a need for a gelation delay between respective gel injections.

The requirement in use of the apparatus as described above for one gel or gel-like substance to gelate before it becomes possible to add a further such substance to the apparatus may be inconvenient in some situations. A solution to this difficulty is provided by the arrangement of FIGS. 3a and 3b in which an additional phaseguide 32 extends parallel to phaseguide 12 from one end of the inside of volume 10 to the other.

Such a phaseguide may be arranged to confine the gel or gel-like substance 29 in sub-volume 14, without disturbing the profile in which a gel or gel like substance is distributed in the volume, while the gel or gel-like substance 31 is being filled into sub-volume 16. This avoids the need for any delay between the filling steps described above.

FIG. 3a illustrates the state of the apparatus during filling of the second sub-volume 16 in this way. In FIG. 3a therefore the gel or gel-like substance 31 does not yet occupy the entirety of the sub-volume; and an exemplary cell 28' is visible in the conduit 22 on its way into the sub-volume 16.

In FIG. 3b the sub-volume 16 is filled and all the cells 28 are inside it.

The phaseguide 32 optionally includes a so-called "engineered overflow" point 33 that for convenience is shown at one end of the phaseguide 32 but could in reality be at any chosen location along its length (and including at one extreme end as shown). Such a feature 33 may be used to induce or promote controlled mixing of the substances in the sub-volumes 14, 16 (or as described herein transport of particles from one sub-volume to another).

Any of the phaseguides disclosed herein could optionally include one or more such engineered overflow features 33.

FIG. 4 shows a third basic version of the invention in which an array 36 of volumes 10, each of which in the embodiment shown includes three of the sub-volumes 14, 16, 17, 18 (although more sub-volumes may be present as desired) is interconnected by fluid-conveying conduits 37.

The central sub-volume 14 of each volume 10 of the array contains e.g. a gel supporting life-based particles. Adjacent to that gel is a perfusion flow in sub-volume 16. The perfusion flow addresses multiple volumes in parallel, starting from the same origin signified schematically by arrow 37a. It is possible then to perfuse multiple examples of the sub-volumes 14 using a "one-shot perfusion" technique in which the single origin simultaneously perfuses a large number of sub-volumes.

The conduits 37 of the perfusion network are arranged such that a partition of perfusion flow is never flushed along two volumes in sequence. This is important in order to avoid contaminating one volume 10 or sub-volume 14 with aspects of another such volume or sub-volume.

A second preferred aspect of the perfusion network is that all flow paths have the same length. This is important in order to guarantee an equal perfusion speed in all chambers.

The challenge of filling such a balanced flow network is solved with the help of phaseguides 38, that typically are as described in WO2010/086179 A2. Each volume has downstream of it in a section of the conduit 37 a phaseguide 38 that assures filling of all volumes. In order to completely fill the downstream conduit 37c that is downstream of the volume 10 in question.

The phaseguide most distal to the downstream end of the common downstream conduit 37c is of lower stability than the other phaseguides along the common downstream conduit 37c. Overflow of this weaker (i.e. less stable) phaseguide therefore occurs first and filling of the downstream conduit commences at its distal part. This sequence of filling is illustrated by FIGS. 4a-4c, with the dark shading indicating the progressive filling of different parts of the conduit network 37 with perfusate. For the avoidance of doubt, relatively upstream and downstream directions herein are defined with reference to the direction of advancement of fluid in the conduits 37, as signified by arrow 37a.

Optionally, the common downstream conduit 37c can be omitted and each volume have its own perfusion outflow unit.

Also optionally, in the case of a weak gel, the pressure on the gel during initial filling can be relieved by introducing a contour phaseguide, similar to phaseguide 37 in FIG. 3.

FIGS. 5a-5c show a more complex one-shot perfusion flow network, in which the conduit geometry of FIG. 4 is embedded in a network of conduits 39, 41 that are higher in hierarchy. In this case additional phaseguides are needed to also fill the common downstream conduit of the higher hierarchy. This is done similar with a similar phaseguide configuration as in FIG. 4, with the exception that the phaseguide of lower stability needs to be of higher stability than the phaseguide of lower stability of the common downstream conduit that is lower in hierarchy.

In other words the hierarchy of the respective conduit/volume arrangement determines the stability of the phaseguides that are needed in it in order to assure a correct filling order even in the case of a complex hierarchy as represented by FIG. 5.

In practical situations the arrays of FIGS. 4 and 5 may be significantly more extensive than the illustrations, which are simplifications for ease of presentation. Careful choice of phaseguide stabilities permits successful operation of even highly extensive networks containing many tens or hundreds of the volumes 10.

Any of the volumes 10 described herein may be associated with one or more excess flow volumes. These are volumes that are connected to the conduits described herein by respective branch conduits.

The purpose of an excess flow volume is to ensure filling of a volume 10 by the correct quantity of fluid, even when a greater quantity potentially could enter it by reason of being present in the associated conduit responsible for filling of the volume.

Any excess flow volume of this kind would include at or near its entrance a phaseguide the stability of which is chosen in order to assure that filling of the volume 10 completes before any excess flow passes into the excess flow volume.

The excess flow volumes are described in more detail in patent application no GB 1103917.9, and typically would include one ore more vents for venting gas in the excess flow volume that is expelled during filling with excess liquid as described.

It is not necessary, in a complex array such as that outlined above, for each volume 10 to be associated with its own excess flow volume. On the contrary, each conduit of the network representing a hierarchical level in the array for instance may have an excess flow volume connected to it by a branch conduit (this being in many cases a sufficient amount of excess flow capacity in the network). As indicated the choice of the stabilities of the phaseguides typically at the entrances to the excess flow chambers determines that they fill in a preferred order, following filling of the volumes proper 10, in the event of an excess flow being present.

Overall the apparatus and methods of the invention represent highly significant advances in the practical applications of so-called microfluidics techniques to topics such as cell cultivation and experimentation.

The listing or discussion of an apparently prior-published document in this specification should not necessarily be taken as an acknowledgement that the document is part of the state of the art or is common general knowledge.

The invention claimed is:

1. Apparatus for processing life-based organic particles including particles selected from the list comprising cells, cellular spheroids, tissues, eukaryotes, micro-organisms, organs or embryos, the apparatus comprising a hollow volume that (a) has at least two confining phaseguides formed inside the volume to define at least first, second and third sub-volumes by separating the at least first, second and third sub-volumes from one another; and (b) includes parts that are relatively upstream and relatively downstream when judged with reference to the movement of a meniscus or a bulk liquid in the volume, the apparatus including at least first, second and third fluid conduits connected to permit fluid communication between the upstream exterior of the volume and a respective said sub-volume; and at least one further conduit connected to permit fluid communication between the downstream exterior of the volume and a said sub-volume, the first said sub-volume containing or chargeable with one or more life-based particles supported in or by a gel or gel-like substance; and the second sub-volume communicating with the first sub-volume so as to permit transport of substances between the first and second sub-volumes and containing or chargeable with at least one gel or gel-like substance, wherein each of the at least two confining phaseguides is a protruding three-dimensional structure, or an area on an internal surface of a volume that is of a differing degree of wettability, located at the boundary between two of the sub-volumes, wherein each of the at least two confining phaseguides spans the complete length, width, or height of the meniscus and represents a pressure barrier for advancement or recession of this meniscus.

2. Apparatus according to claim 1 wherein the third sub-volume communicates with at least the first sub-volume so as to permit transport of substances between the first and third sub-volumes, and wherein the third sub-volume contains or is chargeable with a perfusate.

3. Apparatus according to claim 2 wherein the apparatus is configured to allow the perfusate to flow inside the third sub-volume.

4. Apparatus according to claim 1, wherein the second sub-volume contains one or more cells, cellular spheroids, tissues, eukaryotes, micro-organisms, organs or embryos supported in or by the gel or gel-like substance.

5. Apparatus according to claim 4 wherein the one or more cells, cellular spheroids, tissues, eukaryotes, microorganisms, organs or embryos in the second sub-volume differ from the one or more cells, cellular spheroids, tissues, eukaryotes, microorganisms, organs or embryos in the first sub-volume.

6. Apparatus according to claim 1, including a third confining phaseguide defining a fourth sub-volume inside the volume.

7. Apparatus according to claim 6 wherein the fourth sub-volume communicates with at least the first sub-volume so as to permit transport of substances between the first and fourth sub-volumes, and wherein the fourth sub-volume contains or is chargeable with a perfusate.

8. Apparatus according to claim 7 wherein the apparatus is configured to allow the perfusate to flow inside the third sub-volume.

9. Apparatus according to claim 6 wherein the fourth sub-volume contains or is chargeable with a fluid substance the effect of which on one or more cells, cellular spheroids, tissues, eukaryotes, micro-organisms, organs or embryos in the first volume is required to be investigated.

10. Apparatus according to claim 6 wherein the third and fourth sub-volumes contain or are chargeable with fluid substances that give rise to a concentration gradient in at least the first sub-volume.

11. Apparatus according to claim 9 wherein the fluid substance is or includes a liquid or liquid-based substance.

12. Apparatus according to claim 6 wherein the fourth sub-volume contains or is chargeable with a gas.

13. Apparatus according to claim 1, wherein at least the first sub-volume includes one or more phaseguides that stratify the gel or gel-like substance therein.

14. Apparatus according to claim 1, including connected to at least the first fluid conduit connected to the first sub-volume a further volume; and the apparatus including one or more phaseguides that control the transmission of liquids or liquid-based substances to the further volume such that on charging of the first volume with a predetermined quantity of a gel or gel-like substance any gel or gel-like substance in excess of the predetermined quantity enters the further volume.

15. Apparatus according to claim 1, including at least one contour phaseguide in the volume between the first and second sub-volumes and arranged to maintain a predetermined shape of a boundary of a gel or gel-like substance in at least the first sub-volume.

16. The apparatus of claim 1, wherein the phaseguides do not completely span the cross-section of the chamber.

17. Apparatus for processing life-based organic particles including particles selected from the list comprising cells, cellular spheroids, tissues, eukaryotes, micro-organisms, organs or embryos, the apparatus comprising a hollow volume that (a) has at least two confining phaseguides formed inside the volume to define at least first, second and third sub-volumes by separating the at least first, second and third sub-volumes from one another; and (b) includes parts that are relatively upstream and relatively downstream when judged with reference to the movement of a meniscus or a bulk liquid in the volume, the apparatus including at least first, second and third fluid conduits connected to permit fluid communication between the upstream exterior of the volume and a respective said sub-volume; and at least one further conduit connected to permit fluid communication between the downstream exterior of the volume and a said sub-volume, the first said sub-volume containing or chargeable with one or more life-based particles supported in or by a gel or gel-like substance; and the second sub-volume communicating with the first sub-volume so as to permit transport of substances between the first and second sub-volumes and containing or chargeable with at least one gel or gel-like substance, wherein each of the at least two confining phaseguides is a protruding three-dimensional structure, wherein each of the at least two confining phaseguides spans the complete length, width, or height of the meniscus and represents a pressure barrier for advancement or recession of this meniscus.

* * * * *